United States Patent
Desai et al.

(10) Patent No.: US 10,881,669 B2
(45) Date of Patent: Jan. 5, 2021

(54) INHIBITORS OF THE PLASMODIAL SURFACE ANION CHANNEL AS ANTIMALARIALS

(71) Applicant: The United States of America, as represented by the Secretary, Department of Health and Human Services, Bethesda, MD (US)

(72) Inventors: Sanjay A. Desai, Potomac, MD (US); Ajay D. Pillai, Hyderabad (IN)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/984,956

(22) Filed: May 21, 2018

(65) Prior Publication Data

US 2018/0264003 A1 Sep. 20, 2018

Related U.S. Application Data

(63) Continuation of application No. 15/213,181, filed on Jul. 18, 2016, now Pat. No. 9,974,796, which is a (Continued)

(51) Int. Cl.
*A61K 31/00* (2006.01)
*A61K 31/553* (2006.01)
(Continued)

(52) U.S. Cl.
CPC .......... *A61K 31/553* (2013.01); *A61K 31/165* (2013.01); *A61K 31/4155* (2013.01);
(Continued)

(58) Field of Classification Search
CPC .................................................... A61K 31/554
(Continued)

(56) References Cited

U.S. PATENT DOCUMENTS 2,895,956 A 7/1959 Tuppy
6,602,865 B1 8/2003 Andrasi et al.
(Continued)

FOREIGN PATENT DOCUMENTS

WO WO 00/27851 5/2000
WO WO 02/39987 A2 5/2002
(Continued)

OTHER PUBLICATIONS

PubChem CID 6623258 (Year: 2006).*
(Continued)

*Primary Examiner* — Shengjun Wang
(74) *Attorney, Agent, or Firm* — Leydig, Voit & Mayer, Ltd,

(57) ABSTRACT

Disclosed are inhibitors of the plasmodial surface anion channel (PSAC) inhibitors and the use thereof in treating or preventing malaria in an animal such as a human, comprising administering an effective amount of an inhibitor or a combination of inhibitors. An example of such an inhibitor is a compound of formula I, (I)

(Continued)

or a pharmaceutically acceptable salt thereof, wherein $R^1$ to $R^7$ are as described herein.

9 Claims, 4 Drawing Sheets

Related U.S. Application Data continuation of application No. 14/094,842, filed on Dec. 3, 2013, now Pat. No. 9,394,316, which is a continuation of application No. 13/055,104, filed as application No. PCT/US2009/050637 on Jul. 15, 2009, now Pat. No. 8,618,090.

(60) Provisional application No. 61/083,000, filed on Jul. 23, 2008.

(51) Int. Cl.

| | |
|---|---|
| A61K 31/165 | (2006.01) |
| A61K 31/4155 | (2006.01) |
| A61K 31/423 | (2006.01) |
| A61K 31/4245 | (2006.01) |
| A61K 31/433 | (2006.01) |
| A61K 31/4355 | (2006.01) |
| A61K 31/437 | (2006.01) |
| A61K 31/4439 | (2006.01) |
| A61K 31/4741 | (2006.01) |
| A61K 31/4745 | (2006.01) |
| A61K 31/50 | (2006.01) |
| A61K 31/554 | (2006.01) |
| A61K 45/06 | (2006.01) |
| C07D 403/08 | (2006.01) |
| C07D 498/04 | (2006.01) |
| C07D 263/57 | (2006.01) |
| C07D 281/16 | (2006.01) |
| C07D 413/14 | (2006.01) |
| C07D 417/06 | (2006.01) |
| C07D 491/048 | (2006.01) |
| C07D 513/04 | (2006.01) |
| A61K 31/421 | (2006.01) |

(52) U.S. Cl.
CPC .......... *A61K 31/421* (2013.01); *A61K 31/423* (2013.01); *A61K 31/4245* (2013.01); *A61K 31/433* (2013.01); *A61K 31/437* (2013.01); *A61K 31/4355* (2013.01); *A61K 31/4439* (2013.01); *A61K 31/4741* (2013.01); *A61K 31/4745* (2013.01); *A61K 31/50* (2013.01); *A61K 31/554* (2013.01); *A61K 45/06* (2013.01); *C07D 263/57* (2013.01); *C07D 281/16* (2013.01); *C07D 403/08* (2013.01); *C07D 413/14* (2013.01); *C07D 417/06* (2013.01); *C07D 491/048* (2013.01); *C07D 498/04* (2013.01); *C07D 513/04* (2013.01); *Y02A 50/30* (2018.01)

(58) Field of Classification Search
USPC .................................................. 514/211.04
See application file for complete search history.

(56) References Cited

U.S. PATENT DOCUMENTS

| | | |
|---|---|---|
| 8,618,090 B2 | 12/2013 | Desai et al. |
| 2007/0148185 A1 | 6/2007 | Rathore et al. |

FOREIGN PATENT DOCUMENTS

| | | |
|---|---|---|
| WO | WO 2007/008541 A2 | 1/2007 |
| WO | WO 2008/036139 A2 | 3/2008 |

OTHER PUBLICATIONS

PubChem CID 20885156, Dec. 5, 2007 (Year: 2007).*
PubChem CID 4167767, 2005 (Year: 2005).*
PubChem CID 4167863, 2005 (Year: 2005).*
PubChem CID 20885139, Dec. 2007 (Year: 2007).*
PubChem CID 20885154 Dec. 2007 (Year: 2007).*
Alkhalil et al., "*Plasmodium falciparum* likely encodes the principal anion channel on infected human erythrocytes," *Blood*, 104 (13), 4279-4286 (2004).
Basco et al., "In vitro activities of furoquinoline and acridone alkaloids against Plasmodium falciparum," *Antimicrob. Agents and Chemother.*, 38 (5), 1169-1171 (1994).
Carrico et al. "In vitro and in vivo antimalarial activity of peptidomimetic protein farnesyltransferase inhibitors with improved membrane permeability," Bioorganic & Medicinal Chemistry, 2004, vol. 12, pp. 6517-6526.
Desai et al., "A voltage-dependent channel involved in nutrient uptake by red blood cells infected with the malaria parasite," *Nature*, 406 (6799), 1001-1005 (2000).
Dolabela et al., "In vitro antiplasmodial activity of extract and constituents from Esenbeckia febrifuga, a plant traditionally used to treat malaria in the Brazilian Amazon," *Phytomedicine*, 15 (5), 367-372 (2008).
Johnson, J.D., et al., "Assessment and Continued Validation of the Malaria SYBR Green I-Based Fluorescence Assay for Use in Malaria Drug Screening," *Antimicrobial Agents and Chemotherapy*, Jun. 2007, vol. 51, p. 1926-1933.
Kanaani et al. "Effects of Cinnamic acid derivatives on in vitro growth of plasmodium falciparum and on the permeability of the membrane of malaria-infected erythrocytes," Antimicrobial Agents and Chemotherapy, 1992, Vo. 36, No. 5, pp. 1102-11018.
Kang et al., "Malaria parasites are rapidly killed by dantrolene derivatives specific for the plasmodial surface anion channel," *Mol. Pharmacol.*, 68 (1), 34-40 (2005).
Pillai et al., "High affinity antagonists of the plasmodial surface anion channel inhibit nutrient acquisition by intraerythrocytic malaria parasites," *Biophysical J.*, 1288-Pos Board B344, 272A (2007) abstract.
Wagner et al., "A two-compartment model of osmotic lysis in Plasmodium *falciparum*-infected erythrocytes," *Biophys. J.*, 84 (1), 116-123 (2003).
*WHO Bulletin OMS*, vol. 72, 1994, pp. 307-308 (based on Malaria Prophylaxis for travelers. Weekly epidemiological record, 1993, 68(51): 377-383).
Zhang et al., "A Simple Statistical Parameter for Use in Evaluation and Validation of High Throughput Screening Assays," *J. Biomol. Screen*, 4 (2), 67-73 (1999).
STN International Registry File (Online), RN: CAS 312616-20-9, 1 page.

* cited by examiner

|  | Comp. A | | | | | | | Comp. B | | | | |
|---|---|---|---|---|---|---|---|---|---|---|---|---|
| Compound | 31 | 11 | 35 | 26 | 32 | 33 | 34 | 25 | 21 | 13 | 16 | 36 |
| 24 | Ad | Ad |  | Ad |  |  |  | S | S | S | S | S |
| 31 |  | Ad |  | Ad |  |  |  | S | Ad | S |  | Ad |
| 11 |  |  |  | Ad | Ad | Ad | Ad | S |  | S |  |  |
| 35 |  |  |  |  |  |  |  |  |  |  | S |  |
| 26 |  |  |  |  |  |  |  | S | Ad | S |  |  |
| 32 |  |  |  |  |  |  |  |  |  | S |  |  |
| 33 |  |  |  |  |  |  |  |  |  | S |  |  |
| 34 |  |  |  |  |  |  |  |  |  | S |  |  |
| 25 |  |  |  |  |  |  |  |  | Ad | Ad |  |  |
| 21 |  |  |  |  |  |  |  |  |  | Ad |  |  |
| 13 |  |  |  |  |  |  |  |  |  |  |  |  |

INHIBITORS OF THE PLASMODIAL SURFACE ANION CHANNEL AS ANTIMALARIALS

CROSS-REFERENCE TO A RELATED APPLICATION

This application is a continuation of U.S. patent application Ser. No. 15/213,181, filed Jul. 18, 2016, which is a continuation of U.S. patent application Ser. No. 14/094,842, filed Dec. 3, 2013, now U.S. Pat. No. 9,394,316, which is a continuation of U.S. patent application Ser. No. 13/055,104, filed Feb. 25, 2011, now U.S. Pat. No. 8,618,090, which is a 371 of International Patent Application No. PCT/US2009/050637, filed Jul. 15, 2009, which claims the benefit of U.S. Provisional Application No. 61/083,000, filed Jul. 23, 2008, the disclosures of the '842, '104, '637, and '000 applications are incorporated by reference for all purposes.

BACKGROUND OF THE INVENTION

Malaria, one of the world's most important infectious diseases, is transmitted by mosquitoes and is caused by four species of *Plasmodium* parasites (*P. falciparum, P. vivax, P. ovale, P. malariae*). Symptoms include fever, chills, headache, muscle aches, tiredness, nausea and vomiting, diarrhea, anemia, and jaundice. Convulsions, coma, severe anemia and kidney failure can also occur. It remains a leading cause of death globally, especially amongst African children under 5 years of age. While repeated infections over many years leads to partial immunity in endemic areas, these adults still suffer significant morbidity and loss of productivity. The annual economic loss in Africa due to malaria is estimated at US S12 billion.

There is no effective vaccine currently available for malaria. Treatment has therefore relied primarily on antimalarial drugs such as chloroquine. Because some malaria parasites have acquired resistance to each available antimalarial drug, there is a desire to discover and develop new antimalarials.

BRIEF SUMMARY OF THE INVENTION

The invention provides compounds, pharmaceutical compositions, and use for preventing or treating malaria in animals including humans. The compounds of the invention are represented by formulas I, IV, and V. The compounds of the invention in combination with themselves or with other compounds exhibit synergic killing of parasites.

DETAILED DESCRIPTION OF THE INVENTION

During its approximately 48 h cycle within the human red blood cell (RBC), *P. falciparum* must increase the red blood cell's (RBC's) permeability to a broad range of solutes. Electrophysiological studies identified the plasmodial surface anion channel (PSAC) as the molecular mechanism of these changes. PSAC's functional properties differ from those of known human ion channels. These properties include atypical gating, unique pharmacology, and an unmatched selectivity profile. An unusual property is PSAC's ability to exclude Na+ by more than 100,000-fold relative to Cl− despite the channel's broad permeability to anions and bulky nutrients. This level of exclusion of a single small solute has not been reported in other broadly selective channels; it is essential for parasite survival because a higher Na+ permeability would produce osmotic lysis of infected RBCs in the high Na+ serum.

PSAC plays a central role in parasite nutrient acquisition. Sugars, amino acids, purines, vitamins, and precursors for phospholipid biosynthesis have markedly increased uptake into infected RBCs via PSAC. Many of these solutes have negligible permeability in uninfected RBCs and must be provided exogenously to sustain in vitro parasite growth. PSAC is conserved on divergent plasmodial species, as determined through studies of erythrocytes infected with rodent, avian, and primate malaria parasites. The channel's gating, voltage dependence, selectivity, and pharmacology are all conserved, suggesting that PSAC is a highly constrained integral membrane protein. Its surface location on the erythrocyte membrane offers conceptual advantages over parasite targets buried inside the infected RBC. PSAC's exposed location on infected RBCs forces direct access to antagonists in serum and excludes resistance via drug extrusion. In contrast, drugs acting within the parasite compartment must cross at least three membranous barriers to reach their target; clinical resistance to chloroquine and mefloquine appear to be linked to extrusion from their sites of action. Nearly all available PSAC antagonists inhibit in vitro parasite growth at concentrations modestly higher than those required for channel inhibition.

Accordingly, the invention provides, in an embodiment, a method of preventing malaria or treating an animal afflicted with malaria comprising administering to the animal, preferably a human:

(i) an effective amount of a compound of formula I:

(I)

wherein $R^1$ is hydrogen or alkyl and $R^2$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or $R^2$ is a group of formula (II):

(II)

wherein n=0 to 6;
or $R^1$ and $R^2$ together with the N to which they are attached form a heterocycle of formula III:

(III)

wherein X is N or CH; and
Y is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and
$R^3$-$R^{10}$ are hydrogen or alkyl; or a pharmaceutically acceptable salt thereof;

(ii) an effective amount of a compound of formula IV:

(IV)

wherein
Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;
$R^a$ is hydrogen, alkyl, or alkoxy;
P is a bond, alkyl, alkoxy, $(CH_2)_r$, or $(CH_2O)_s$, wherein r and s are independently 1 to 6;
Q is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and
when P is alkyl or alkoxy, Q is absent;
or a pharmaceutically acceptable salt thereof;

(iii) an effective amount of a compound of formula V:

(V)

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;
$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof; or

(iv) an effective amount of any combination of the compounds of formulas I, IV, and V, or pharmaceutically acceptable salts thereof.

The present invention also provide the use of (i) a compound of formula I:

(I)

wherein R is hydrogen or alkyl and $R^2$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or $R^2$ is a group of formula (II):

(II)

wherein n=0 to 6;
or $R^1$ and $R^2$ together with the N to which they are attached form a heterocycle of formula III:

(III)

wherein X is N or CH; and
Y is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and
$R^3$-$R^{10}$ are hydrogen or alkyl; or a pharmaceutically acceptable salt thereof;

(ii) a compound of formula IV:

(IV)

wherein
Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;

$R^a$ is hydrogen, alkyl, or alkoxy;

P is a bond, alkyl, alkoxy, $(CH_2)_r$, or $(CH_2O)_s$, wherein r and s are independently 1 to 6;

Q is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and when P is alkyl or alkoxy, Q is absent;
or a pharmaceutically acceptable salt thereof;

(iii) a compound of formula V:

(V)

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;

$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof; or (iv) any combination of the compounds of formulas I, IV, and V, or pharmaceutically acceptable salts thereof;

in the preparation of a medicament for preventing malaria or treating an animal afflicted with malaria.

The present invention further provides a pharmaceutical composition comprising a pharmaceutically acceptable carrier and (i) a compound of formula I:

(I)

wherein $R^1$ is hydrogen or alkyl and $R^2$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or $R^2$ is a group of formula (II):

(II)

wherein n=0 to 6;

or $R^1$ and $R^2$ together with the N to which they are attached form a heterocycle of formula III:

(III)

wherein X is N or CH; and

Y is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and $R^3$-$R^{10}$ are hydrogen or alkyl; or a pharmaceutically acceptable salt thereof;

(ii) a compound of formula IV:

(IV)

wherein

Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;

$R^a$ is hydrogen, alkyl, or alkoxy;

P is a bond, alkyl, alkoxy, $(CH_2)_r$, or $(CH_2O)_s$, wherein r and s are independently 1 to 6;

Q is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and when P is alkyl or alkoxy, Q is absent;

or a pharmaceutically acceptable salt thereof;

(iii) a compound of formula V:

(V)

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;

$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof; or (iv) any combination of the compounds of formulas I, IV, and V, or pharmaceutically acceptable salts thereof.

Referring now to terminology used generically herein, the term "alkyl" implies a straight or branched alkyl moiety containing from, for example, 1 to 12 carbon atoms, preferably from 1 to 8 carbon atoms, more preferably from 1 to 6 carbon atoms. Examples of such moieties include methyl, ethyl, propyl, isopropyl, n-butyl, sec-butyl, isobutyl, tert-butyl, pentyl, isoamyl, hexyl, octyl, dodecanyl, and the like.

The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein n=1, 2, or 3.

The term "heterocyclic" means a cyclic moiety having one or more heteroatoms selected from nitrogen, sulfur, and/or oxygen. Preferably, a heterocyclic is a 5 or 6-membered monocyclic ring and contains one, two, or three heteroatoms selected from nitrogen, oxygen, and/or sulfur. Examples of such heterocyclic rings are pyrrolinyl, pyranyl, piperidyl, tetrahydrofuranyl, tetrahydrothipheneyl, and morpholinyl.

The term "alkoxy" embraces linear or branched alkyl groups that are attached to a an ether oxygen. The alkyl group is the same as described herein. Examples of such substituents include methoxy, ethoxy, t-butoxy, and the like.

The term "halo" as used herein, means a substituent selected from Group VIIA, such as, for example, fluorine, bromine, chlorine, and iodine.

For the purpose of the present invention, the term "fused" includes a polycyclic compound in which one ring contains one or more atoms preferably one, two, or three atoms in common with one or more other rings.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any subrange or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In accordance with an embodiment of the invention, $R^3$ in formula I is hydrogen. In accordance with the above embodiments, $R^4$-$R^7$ in formula I are hydrogen. In an example, $R^1$ in formula I is hydrogen and $R^2$ is a group of formula II, wherein n=1 to 6, preferably n=2 to 4.

In accordance with an embodiment of the invention, wherein $R^1$ and $R^2$ together with the N to which they are attached form a heterocycle of formula III. For example, X in formula III is N. In accordance with the invention, in formula III, Y is aryl which is optionally substituted with one or more substituents selected from the group consisting of halo, hydroxyl, nitro, cyano, amino, alkyl, alkoxy, aminoalkyl, alkylamino, alkylcarbonyl, alkoxycarbonyl, aminocarbonyl, and formyl. For example, in formula III, Y is phenyl, which is optionally substituted with one or more substituents selected from the group consisting of halo, hydroxyl, nitro, cyano, amino, alkyl, alkoxy, aminoalkyl, alkylamino, alkylcarbonyl, alkoxycarbonyl, aminocarbonyl, and formyl, specifically, Y is phenyl or phenyl substituted with one or more substituents selected from the group consisting of methyl, chloro, fluoro, and methoxy.

In accordance with any of the embodiments above, the compound of formula I is:

-continued

8

In accordance with another embodiment of the invention, X in formula III is CH. In a particular embodiment, Y is arylalkyl or heterocyclic, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Illustratively, Y is benzyl or piperidinyl, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Examples of specific compounds of formula I are:

9 and

10

In another embodiment of the invention, $R^1$ in formula I is hydrogen and $R^2$ is arylalkyl, optionally substituted on the aryl with a substituent selected from the group consisting of halo, hydroxyl, nitro, cyano, amino, alkyl, aminoalkyl, alkylamino, alkylcarbonyl, and formyl. As an example, $R^2$ is arylalkyl, e.g., phenylalkyl such as phenyl butyl. A specific example of such a compound of formula I is:

11

In accordance with an embodiment of the invention, a specific example of a compound of formula II is:

12

In accordance with another embodiment of the invention, in the compound of formula IV, P is a bond or $(CH_2O)_s$, and Q is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In accordance with an embodiment, wherein Z is a group having one or more 4-7 membered rings, wherein at least one of the rings has at least one heteroatom selected from the group consisting of O, S, and N; and when two or more 4-7 membered rings are present, they may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In the above embodiment, Z is a group having one or two 4-7 membered rings, wherein at least one of the rings has at least one heteroatom selected from the group consisting of O, S, and N; and when two 4-7 membered rings are present, they may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In a specific embodiment of the formula IV, Q is an aryl group, optionally substituted with an alkoxy group or Q is a heterocyclic group which is saturated or unsaturated. For example, Q is aryl such as phenyl or naphthyl.

Examples of compounds of formula IV are:

13

14

In accordance with an embodiment of the invention, in the compound of formula IV, Q is a heteroaromatic group, e.g., pyridyl. An example of such a compound is:

In accordance with another embodiment of the invention, in the compound of formula IV, P is an alkyl group and Q is absent. Examples of such compounds are:

In accordance with another embodiment of the invention, in the compound of formula V, $R^{13}$ is alkyl or alkoxy and $R^{14}$ and $R^{15}$ are hydrogen. In a particular embodiment, $R^{13}$ is methyl or methoxy.

In the above embodiments of the compound of formula V, specifically, $R^{11}$ is alkyl and $R^{12}$ is alkyl, cycloalkyl, or aryl, wherein said aryl is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl. In a particular embodiment, $R^{12}$ is alkyl, cycloalkyl, or aryl, wherein said aryl is optionally substituted with one or more alkyl and/or alkoxy substituents.

Examples of compounds of formula V are:

27

In accordance with an embodiment of the invention, in compound of formula V, $R^{11}$ is hydrogen and $R^{12}$ is cycloalkyl or aryl, which is optionally substituted with one or more alkyl and/or alkoxy substituents. Exemplary compounds of formula V are:

28 or

29

In accordance with the invention, an effective amount of any suitable combination compounds can be administered, for example, a combination of compounds of formulas I and IV, compounds of formulas I and V, compounds of formulas IV and V, or compounds of formulas I, IV, and V, or pharmaceutically acceptable salts thereof, is administered. A notable feature of the invention is that it provides synergy—enhanced killing of the parasite, when a combination of two or more compounds are employed. The extent of killing is greater than the sum of the individual killings.

In accordance with the invention, advantageously, a compound selected from the group consisting of:

24

,

11

,

26

, and

30 or a pharmaceutically acceptable salt thereof is administered in combination with

15 or a pharmaceutically acceptable salt thereof.

In accordance with an embodiment of the invention,

24 or pharmaceutically acceptable salt thereof is administered in combination with

18 or a pharmaceutically acceptable salt thereof.

In accordance with an embodiment of the invention,

24 or a pharmaceutically acceptable salt thereof is administered in combination with

21 or a pharmaceutically acceptable salt thereof.

In accordance with an embodiment of the invention, any of the compounds described above can be administered advantageously in combination, i.e., simultaneously or sequentially, with a further compound of the formula:

32

33

34

35 , or

36 wherein these further compounds are not part of formula I, IV, or V.

The compounds of the invention can be prepared by suitable methods as would be known to those skilled in the art or obtained from commercial sources such as ChemDiv Inc., San Diego, Calif. or Peakdale Molecular Limited, High Peak, England. See also WO 00/27851 and U.S. Pat. Nos. 6,602,865 and 2,895,956.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The amount or dose of a compound of the invention or a salt thereof, or a composition thereof should be sufficient to affect a therapeutic or prophylactic response in the mammal. The appropriate dose will depend upon several factors. For instance, the dose also will be determined by the existence, nature and extent of any adverse side effects that might accompany the administration of a particular compound or salt. Ultimately, the attending physician will decide the dosage of the compound of the present invention with which to treat each individual patient, taking into consideration a variety of factors, such as age, body weight, general health, diet, sex, compound or salt to be administered, route of administration, and the severity of the condition being treated. Typical doses might be, for example, 0.1 mg to 1 g daily, such as 5 mg to 500 mg daily.

The following example further illustrates the invention but, of course, should not be construed as in any way limiting its scope.

Example 1

This example demonstrates the methodology employed to identify PSAC antagonists and characterize their interactions with PSAC. Methodologies include, but are not limited to, high-throughput screening of antagonists, electrophysiology, and in vitro parasite growth inhibition assays.

A high-throughput screen for antagonists of the plasmodial surface anion channel (PSAC) was developed. This screen is based on a quantitative light scattering assay for PSAC activity (Wagner et al., Biophys. J. 84:116 (2003)). This light scattering assay measures changes in turbidity resulting from osmotic swelling and lysis of P. falciparum-infected cells in solutes with high permeability through PSAC, but negligible permeability in uninfected erythrocytes.

Synchronous in vitro cultures of P. falciparum (Indo 1 isolate) were harvested at the mature trophozoite stage and enriched to >95% parasitemia by percoll-sorbitol density gradient centrifugation. Cells were washed and resuspended in phosphate buffer (150 mM NaCl, 20 mM $NaH_2PO_4$, pH 7.5). The cell suspension was then dispensed into 384-, 1536-, or 3456-well plates. Individual compounds (DMSO stock solutions) were pinned from random small molecule libraries into each well. Osmotic lysis was initiated by addition of 280 mM sorbitol, 20 mM Na-HEPES, pH 7.4 to at least four times the volume of the original cell suspension. In plate positive and negative controls were phosphate buffer with 2 mM furosemide and sorbitol with no compound, respectively. Transmittance readings were performed at timed intervals at 700-750 nm, based on the plate format. Hematocrit, total volume, final compound and DMSO concentrations, and time to each reading were optimized, yielding Z' statistics greater than 0.7, where a perfect noise-free assay had a Z' of 1.0 (Zhang et al., J. Biomol. Screen. 4:67 (1999)). Timed readings in this endpoint assay permitted accurate estimation of antagonist affinity in a high-throughput format. Re-test rates for hits were generally >95%.

The identified PSAC antagonists were confirmed and mechanism of action determined with cell-attached and whole-cell patch-clamp recordings on P. falciparum-infected human erythrocytes. These were obtained as described in (Alkhalil et al., Blood 104:4279 (2004)) using symmetric bath and pipette solutions of 1,000 mM choline-Cl, 115 mM NaCl, 10 mM $MgCl_2$, 5 mM $CaCl_2$, 20 mM Na-HEPES, pH 7.4. This hypertonic solution increased the signal-to-noise ratio for single PSAC detection by permitting higher rates of Cl$^-$ flux through open channels and by reducing electrical noise from the pipette. Recordings used quartz pipettes pulled to tip diameters <0.5 µm and resistances of 1-3 MΩ in the recording solution. Seal resistances were >100 GΩ. Antagonists were added to either bath or pipette compartments to determine mechanism of PSAC inhibition, whether the agent inhibits from the intracellular or extracellular face, and stoichiometry of interaction with PSAC. All recordings were low-pass filtered at 5 kHz (8-pole Bessel) and digitized at 100 kHz. All-points histograms and other analyses were carried out with home-written code.

Parasite killing by identified PSAC antagonists was evaluated using a SYBR Green 1-based fluorescence assay for parasite nucleic acid in 96-well format. Synchronous parasite cultures were seeded at 0.2-0.5% parasitemia and 5% hematocrit in RPMI 1640 supplemented with 25 mM HEPES, 2-10% serum, 50 mg/L hypoxanthine, and PSAC antagonists at selected concentrations. Cultures were maintained for 3 days at 37° C. in 5% $O_2$, 5% $CO_2$. The plates were then subjected to freeze-thaw before addition of SYBR Green I at twice the manufacturer's recommended final concentration, incubation in the dark for 30 min, and measurement of fluorescence (excitation/emission at 485/528 nm). For each antagonist concentration, the mean of triplicate measurements was calculated after subtraction of background fluorescence from cultures killed by 20 µM chloroquine, a known antimalarial agent.

Table 1 shows the growth inhibition data and PSAC inhibition data for compounds of the invention in accordance with embodiments of the invention.

TABLE 1

| Compound Number | In vitro growth inhibitory $IC_{50}$ (µM) | PSAC inhibition $IC_{50}$ (µM) |
|---|---|---|
| 11 | 3.00 | 0.08 |
| 10 | 3.01 | 0.82 |
| 9 | 6.90 | 1.85 |
| 2 | 1.00 | 0.13 |
| 5 | 1.33 | 0.72 |
| 3 | 0.67 | 0.07 |
| 13 | 3.85 | 0.60 |
| 22 | 21.46 | 55.00 |
| 19 | 2.74 | 2.99 |
| 18 | 2.14 | 0.26 |
| 16 | 4.98 | 2.17 |
| 23 | 36.73 | 55.00 |
| 20 | 21.59 | 58.00 |
| 17 | 39.01 | 8.22 |
| 15 | 6.00 | |
| 21 | 10.00 | |
| 24 | 9.00 | 0.09 |
| 25 | 4.00 | 0.03 |
| 26 | 6.90 | 0.03 |
| 32 | 3.00 | 0.03 |
| 33 | >20 | 0.08 |
| 34 | 15.00 | 0.17 |

Figure 1:
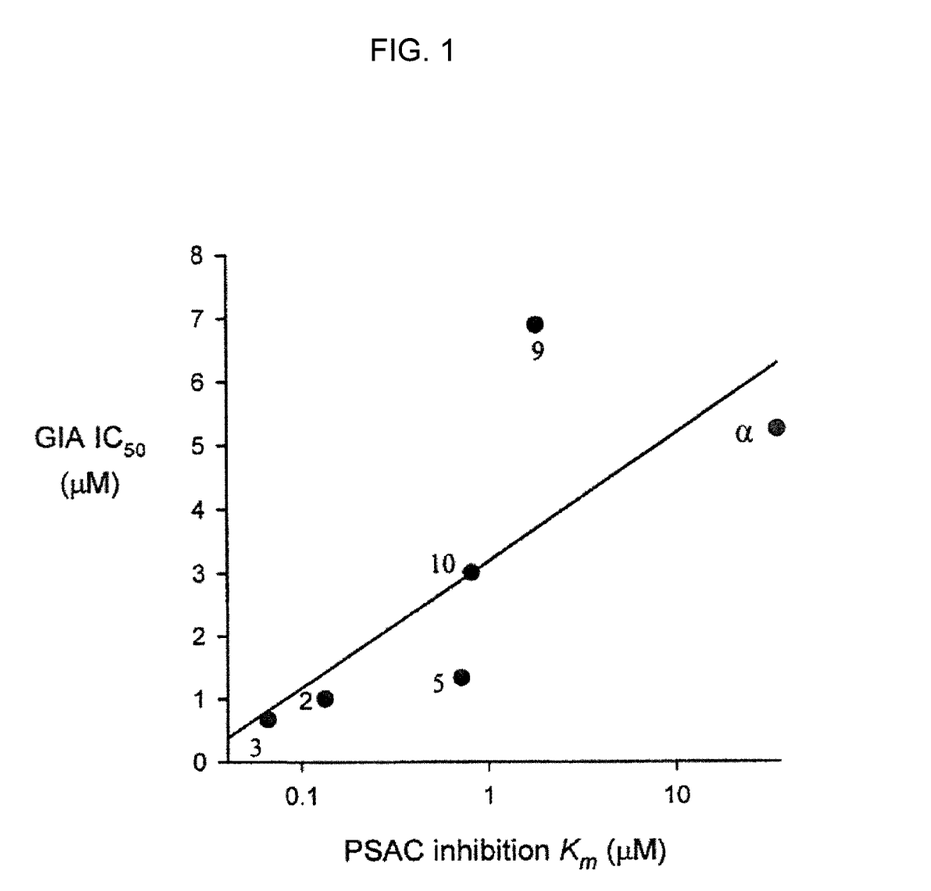
FIG. 1 depicts the correlation of parasite growth inhibitory effect with PSAC inhibition for compounds in accordance with an embodiment of the invention. The formula of compound α is.
Figure 2:
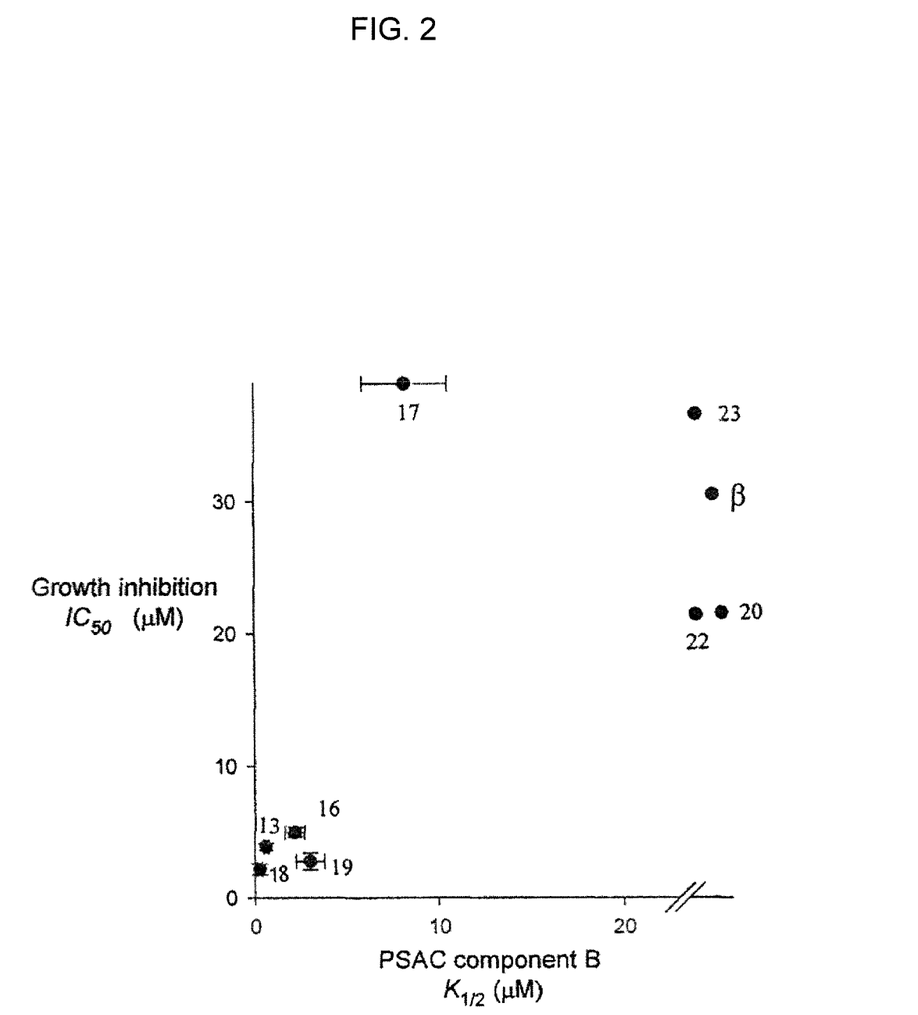
FIG. 2 depicts the correlation of parasite growth inhibitory effect with PSAC inhibition for compounds in accordance with another embodiment of the invention. The formula of compound β is.

FIGS. 1 and 2 show that parasite growth inhibition correlates with PSAC inhibition for compounds in accordance with embodiments of the invention.

Figures 3A, 3B:
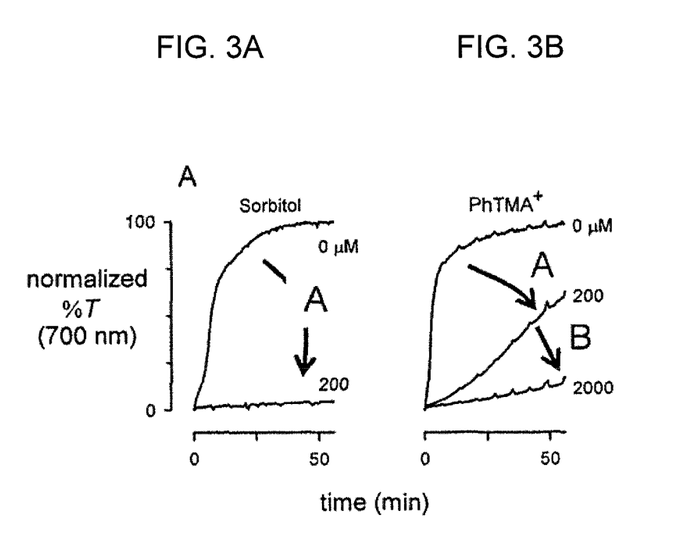
FIG. 3A depicts the kinetics of PSAC-mediated osmotic lysis in isotonic solutions of sorbitol with indicated micromolar concentrations of furosemide, a known PSAC antagonist. "A" represents channel component A.
FIG. 3B depicts the kinetics of PSAC-mediated osmotic lysis in isotonic solutions of phenyltrimethylammonium chloride (PhTMA$^+$Cl$^-$) with indicated micromolar concentrations of furosemide. "A" and "B" represent channel components A and B.

The second type of target validation study involved growth inhibition by combinations of two distinct categories of PSAC antagonists. These antagonist categories were identified in the two separate high-throughput screens. The two screens differed in the permeant solute used to produce PSAC-mediated osmotic lysis and were based on differences in inhibitor affinity identified through basic research studies of PSAC. While sorbitol uptake via PSAC is effectively inhibited by 200 µM furosemide (FIG. 3A), uptake of phenyltrimethyl ammonium (PhTMA$^+$) requires significantly higher concentrations of furosemide and other known antagonists (FIG. 3B). Biophysical studies that included transport of permeating solute mixtures, temperature effects, and electrophysiological correlates suggest that this observation reflects two separate routes solutes may take through PSAC. Here, these routes are referred to as channel components "A" and "B". The two high-throughput screens were therefore designed to identify specific inhibitors of each component.

Figure 3C:
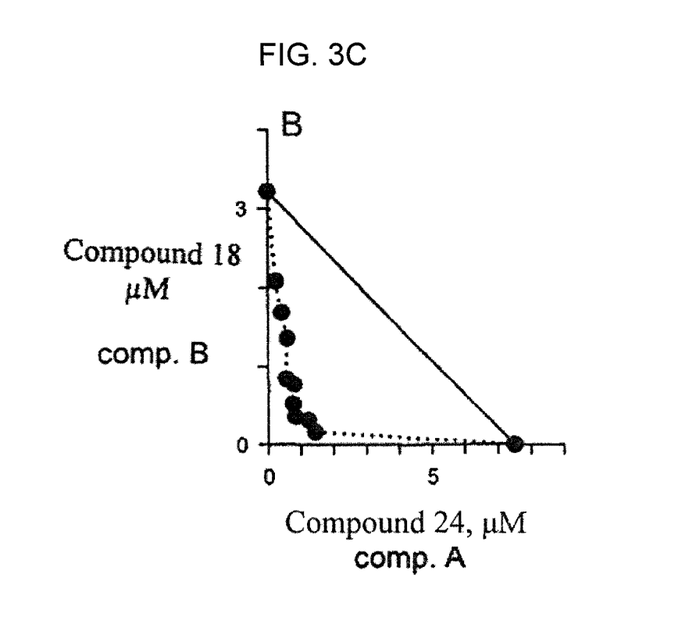
FIG. 3C depicts an isobologram for parasite killing by combinations of a component B antagonist (compound 18) and a component A antagonist (compound 24). Symbols represent compound mixtures that produce 50% parasite killing. The solid line represents the line of additive killing. The data points below the line of additive killing indicates synergistic parasite killing by the combination of antagonists.

FIG. 3C is an isobologram for parasite killing by combinations of compound 18 (a component B antagonist) and compound 24 (a component A antagonist). The symbols represent compound mixtures that produce 50% parasite killing. The solid line represents the line of additive killing. The data points are all below the solid line, indicating synergistic parasite killing by this combination.

Figure 4:
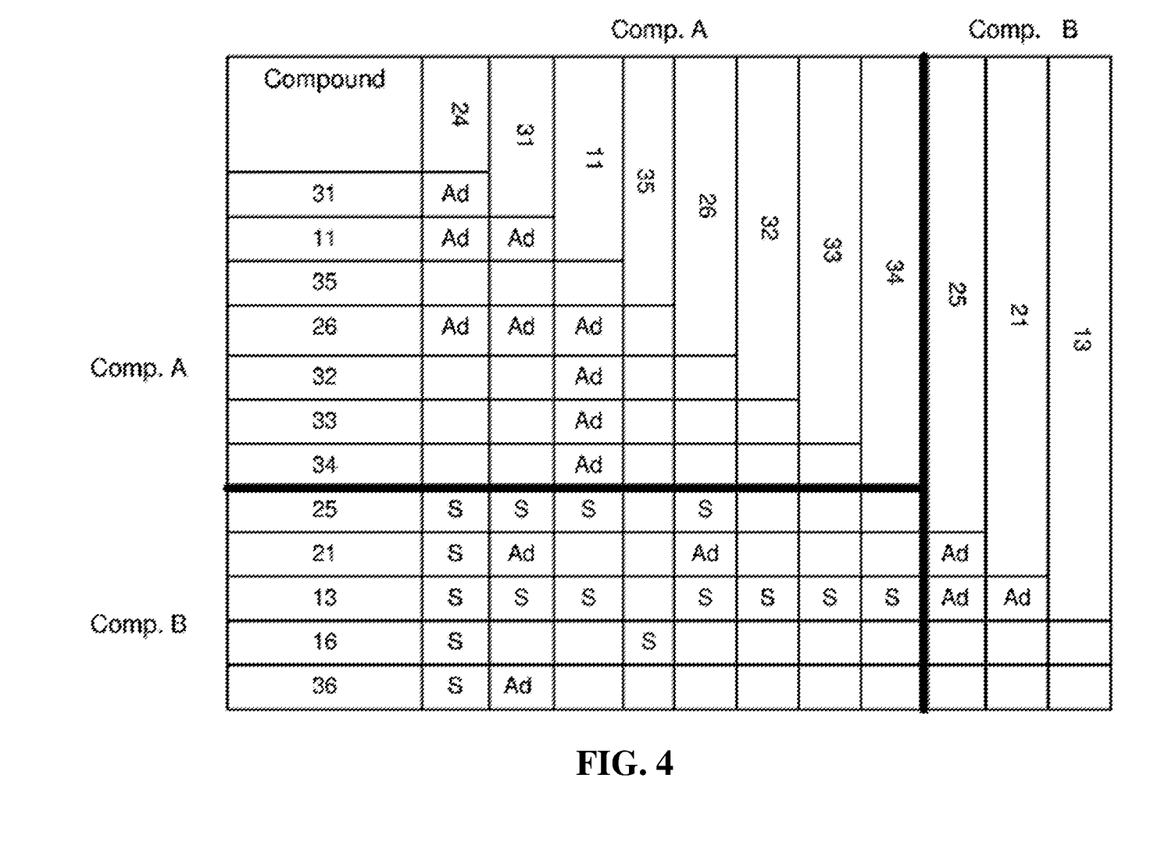
FIG. 4 shows results of in vitro parasite growth inhibition studies using combinations of two component A antagonists (above horizontal divider line), two component B antagonist (right of vertical divider line), or mixtures using an antagonist for each component (bottom left quadrant). Additive and synergistic parasite killing are indicated by "Ad" and "S", respectively.

FIG. 4 shows results of in vitro parasite growth inhibition studies using combinations of two component A antagonists (above horizontal divider line), two component B antagonist (right of vertical divider line), or mixtures using an antagonist for each component (bottom left quadrant). Additive and synergistic parasite killing are indicated by "Ad" and "S", respectively.

While antagonists from both screens kill parasites at low micromolar concentrations when applied individually, there was marked synergistic killing when a component A antagonist was combined with a component B antagonist (FIG. 3C). Multiple permutations of antagonist combinations have been evaluated. Despite the use of several different chemical scaffolds, these experiments revealed that nearly all combinations that inhibit both channel components produce synergistic parasite killing. In contrast, combinations using two antagonists of the same channel component produced only additive parasite killing (FIG. 4). These finding provide independent validation of PSAC as a drug target and support our biophysical model of transport via two routes through the channel.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand use of referring individually to each separate value falling within the range, unless otherwise indicated herein, and each separate value is incorporated into the specification as if it were individually recited herein. All uses described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising a pharmaceutically acceptable carrier and

(i) a compound selected from:

-continued

, and wherein the pharmaceutical composition is a formulation suitable for oral administration selected from capsules, sachets, tablets, lozenges, and troches, each containing a predetermined amount of the compound as solid or as granules.

2. The pharmaceutical composition of claim 1, wherein the compound is:

3. The pharmaceutical composition of claim 1, wherein the compound is:

4. The pharmaceutical composition of claim 1, wherein the compound is:

5. The pharmaceutical composition of claim 1, wherein the compound is:

6. The pharmaceutical composition of claim 1, wherein the compound is:

7. The pharmaceutical composition of claim 1, wherein the compound is:

8. The pharmaceutical composition of claim 1, wherein the compound is:

9. The pharmaceutical composition of claim 1, wherein the compound is:

* * * * *